United States Patent [19]

Amate

[11] Patent Number: Plant 7,303

[45] Date of Patent: Aug. 21, 1990

[54] *AGAPANTHUS ELAINE* PLANT

[76] Inventor: Archie A. Amate, 15662 Sunflower La., Huntington Beach, Calif. 92647

[21] Appl. No.: 313,703

[22] Filed: Feb. 21, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Francis X. LoJacono

[57] ABSTRACT

An *Asapanthus elaine* plant which is defined by its exceptional vigor and having large heads of dark blue-violet flowers on scapes well exceeding the relatively compact foliage, and when in flower, will reach an overall height of 13 dm, and wherein the present plant differs from other Agapanthus selections in that it is provided with large dense umbel of very dark violet-blue flowers in combination with very broad robust foliage, with the flowers ranging from 4.0–4.2 cm in length and 2.2–2.4 cm across at the apex thereof when fully expanded.

2 Drawing Sheets

The present invention relates specifically to a new and distinct variety of the Agapanthus plant family. This new cultivar is known as an *Agapanthus elaine* and was discovered by me as a seedling having the possible outcrossed parentage involving *A. africanus* and *A. praecox* ssp. orientalis. However, the seed and pollen parents can not be identified with certainty. It was discovered by me in 1978 among a group of cultivated plants, and at which time various seedlings were selected from crosses of hybrid seedling plants from which I hoped to develop a stock of commercial plants suitable for propagation and sale in the United States. The present plant has been successfully asexually reproduced by me, through the means of using tissue culture from the selected seedling under appropriate conditions at the Twyford Laboratories in Santa Paula, Calif. The present variety has been asexually reproduced during the last ten years since its discovery, and these asexual reproductions have continuously exhibited the following characteristics which clearly show that the new.

My new and distinct cultivar which will hereinafter be known as *Agapanthus elaine,* is readily distinguishable from other Agapanthus cultivars and was surprisingly found to have exceptional vigor in its larger dense umbel of very dark blue-violet (Violet Blue Group 43A) flowers in combination with its very robust foliage, which includes up to 16 distichously arranged leaves that rise from the ground, spreading, with the leaves being united at the base thereof to define a stout pseudotrunk. The vein pattern above and below the leaf blades are well defined and conspicuous, wherein each leaf blade is formed having closely spaced veins. These veins are spaced about 2 mm apart near the center of the blade and become progressively more closely spaced toward the margins thereof. Mature leaves grow to an approximate length of 60 cm and range from 5.6 to 6.3 cm wide, with their upper and lower surfaces having a medium green colour (Green Group 143) with a some what glaucous cast.

Under closer observation, this unusual Agapanthus plant, that was developed from the tissue culture thereof, appeared to have a size quite different and unique from all the other surrounding Agapanthus plants. That is, the present plant is medium in height in comparison to the general Agapanthus in that it will reach between 10 and 13 dm in height. Thus, with continued close observations of this unique medium size plant and progeny thereof I was convinced that it represented a new and distinct variety unlike any other plant formerly known to me or previously reported or described in published literature, as evidenced by the combination of features which are outstanding in my new plant.

There are two accompanying drawings present in the form of full color photographs, one of which is employed to show the overall view thereof, wherein the medium length stems are defined having larger than normal dark blue-violet flowers (Violet-Blue Group 93A R.H.S. Colour Chart) on scapes that exceed the relatively compact distichous foliage. One of the photographs shows the dense floral arrangement of the large bouquet-like inflorescence which is defined by larger than normal, very dark blue-violet flowers (Violet-Blue Group 93A).

In the following description of the plant are taken from The Royal Horticultural Society Colour Chart.

THE PLANT

General characteristics: The plant is an evergreen perennial herb with thick, heavy rhizomes forming clumps by offsets.

Rhizome: Cylindrical, branched, with many fleshy roots.

Dimensions: When in flower, the plant may reach a height of 13 dm.

FOLIAGE

General: The leaves are numerous (up to 16), in a distichous arrangement arising from near the ground, spreading, and united at the base into a stout pseudostem.

Size: Mature leaves are approximately 60 cm long and range from 5.6 to 6.3 cm wide.

Color: The upper and lower surfaces of the leaves are medium green (Green Group 143) with a slight glaucous cast, with the extreme margins thereof being translucent pale green (Green Group 143C).

Shape: The leaves are strap-shaped (lorate) and slightly narrowed below, deeply channeled below grading to shallowly channeled above, rounded to acute at the apex, with the tip being slightly offset from the center thereof.

Venation: Apparent above, conspicuous below the leaf blade with the veins being closely spaced, about 2 mm apart near the center of blade becoming progressively more closely spaced toward margins.

Arrangement: Distichous.

Texture: The texture of the leaves is thick-textured but pliable and not brittle. Torn leaf portions bear long streaming fibers.

INFLORESCENCE

Arrangement: Flowers are numerous, crowded in false umbels atop tall, slender scapes emerging from the center of the leaves and much exceeding them in height.

Umbel: To 20 cm across and 15 cm high.

Scapes: Scrapes are glaucescent, and being more or less rounded in cross section, reaching a maximum height of 11.1 dm. About 2.5 cm thick at the base and 1.2 cm thick at apex.

Bracts: Inflorescence subtended by thin, bracts which soon dry and fall away leaving a conspicuous broad corky scar at the top of the scape.

FLOWERS

General: Flowers hypogynous, long-pedicillate, very numerous, out-facing to having a declination of approximately 40 degrees to its supporting stem infundubular-salverform, slightly zygomorphic, from a cylindrical base, about 2 cm long.

Buds: Narrowly oblanceolate in outline.

Dimensions: Individual flowers range from 4.0 to 4.2 cm long and at the apex range from 2.5 to 2.7 cm high by 2.2 to 2.5 across.

Pedicels: Each flower in the inflorescence is borne on a thin pedicel ranging in length from 7.6 to 8.0 cm.

Tepals: Each flower is composed of six segments arranged in two whorls of three, an narrower outer trio and a broader inner trio. These are flaring and overlapping along their margins.

Pigmentation: Tepals with prominent dark (Violet-Blue Group 93A) midribs ventrally from the apex almost to the base of the tube appearing light along the central line. Extreme margins or edges ventrally equally deeply pigmented. Lowest $\frac{1}{3}$ to $\frac{1}{2}$ within whitish between darker margins and midveins, grading to medium violet-blue (Violet-Blue Group 94A) above. Ventral surfaces are more evenly colored with lighter portions corresponding to whitish portions within.

Outer segments: Narrowly oblanceolate, with raised midrib at dorsal apex forming a heavy mucro, to 4.1 cm long and 8 mm wide.

Inner segments: Spathulate-oblanceolate with apical margins finely and irregularly crenulate-undulate, 4.0 to 4.2 cm long and 10 mm wide.

Stamens: Six, adnate to the floral tube, declinate along lowest tepal, approximately equaling tepals but one or more exserted. Filaments medium violet-blue above (Violet-Blue Group 94A), white at base, Pollen yellow, anthers later black.

Pistil: Style included in corolla, declinate without defined stigma, pale violet-blue above (Violet-Blue Group 94A), white below, about 2.5 cm long. Ovary greenish-yellow, trigonous, 1.2 cm long by 3 mm broad at apex.

Fruits: Not seen

Notes: Offsets arising from among leaves toward center of the plant. Two seen developing from one plant.

I claim:

1. A new and distinct variety of Agapanthus plant substantially as shown and described characterized by its ability to reach a height of 13 dm when in flower, which includes slender glaucesent scape that reach to a maximum height of 11.1 dm, and having a hardy upright growth habit along with prominent dark blue-violet flowers which are slightly zygomorphic from the cylindrical base and with each flower being composed of six segments arranged in two whorls of three defined by a narrower outer pair, the flowers ranging from 4.0–4.2 cm long, and 2.2–2.5 cm across at the apex when fully expanded with the leaves being formed having veins closely spaced about 2 mm apart near the center of the leaves which are thick-textured but pliable and reach a maximum length of 60 cm long and range from 5.6–6.3 cm wide.

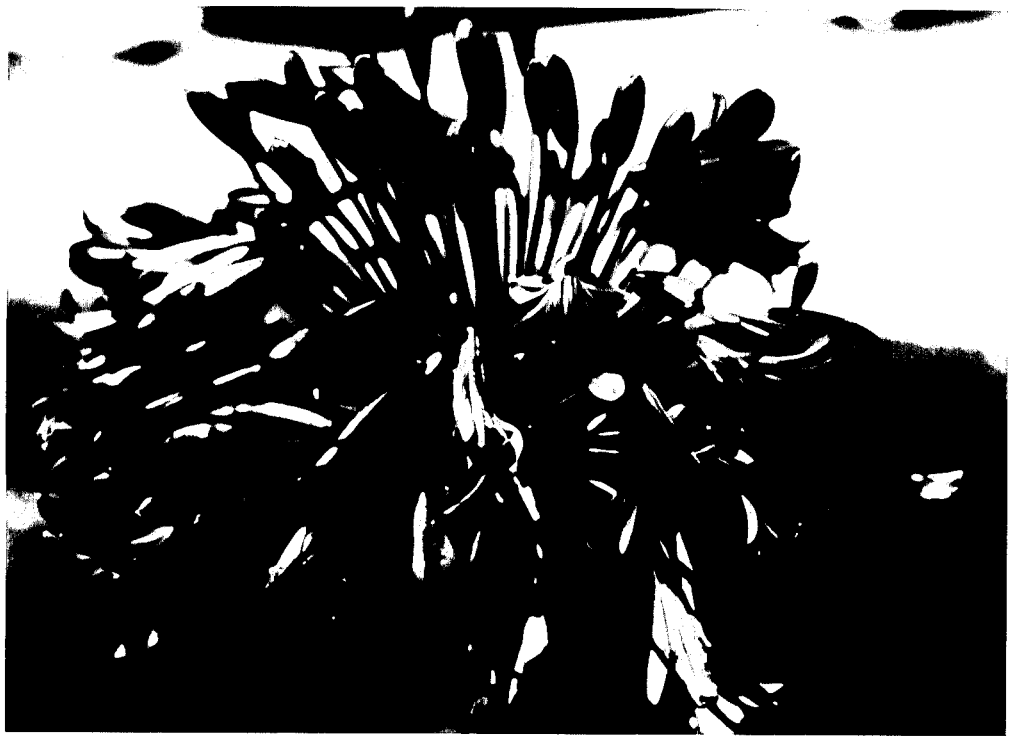

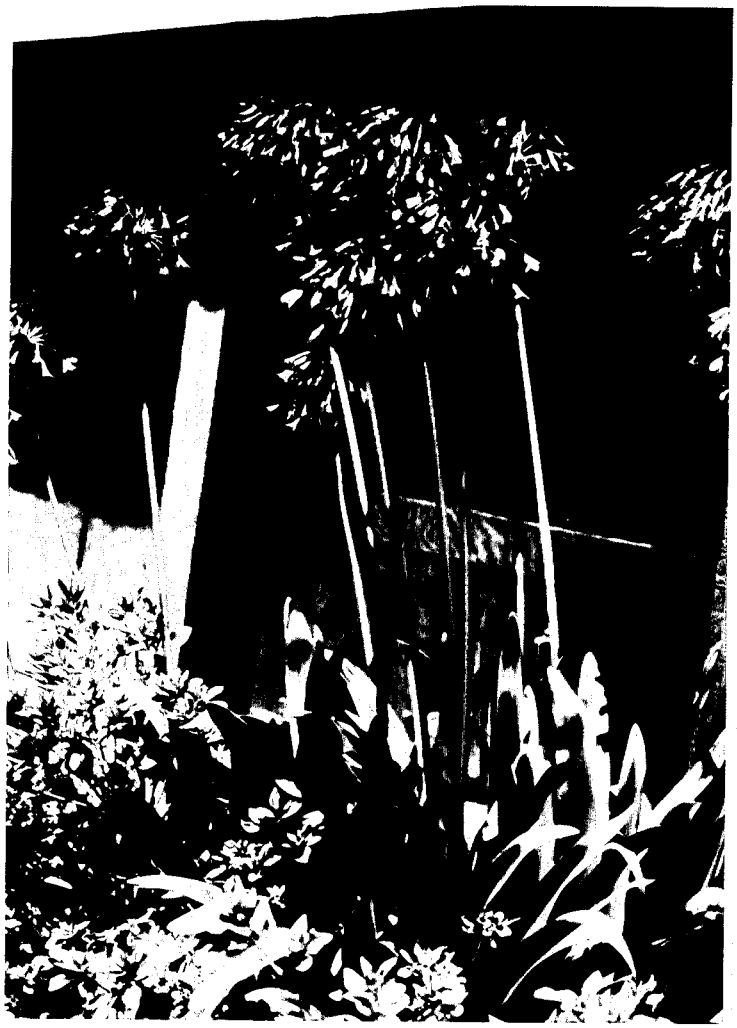

* * * * *